United States Patent [19]

Holland

[11] Patent Number: 5,596,155
[45] Date of Patent: Jan. 21, 1997

[54] GAS SAMPLING PROBE

[75] Inventor: Ernest Holland, Daventry, England

[73] Assignee: V.L. Churchill Ltd., England

[21] Appl. No.: 373,185

[22] PCT Filed: Jul. 12, 1993

[86] PCT No.: PCT/GB93/01449

§ 371 Date: Jan. 17, 1995

§ 102(e) Date: Jan. 17, 1995

[87] PCT Pub. No.: WO94/02824

PCT Pub. Date: Feb. 3, 1994

[30] Foreign Application Priority Data

Jul. 17, 1992 [GB] United Kingdom ............... 9215295

[51] Int. Cl.$^6$ ..................................... G01N 1/22
[52] U.S. Cl. ................... 73/864.73; 73/863.81; 73/863.82; 73/23.33
[58] Field of Search ............ 73/864.73, 863.81, 73/23.33, 863.82, 863.85, 863.41, 863.43, 863.51, 863.58, 23.2, 23.31, 864.31

[56] References Cited

U.S. PATENT DOCUMENTS

| 2,648,976 | 8/1953 | Bur | 73/863.82 X |
|---|---|---|---|
| 2,935,866 | 5/1960 | Schmidt et al. | 73/864.73 X |
| 3,381,409 | 5/1968 | Lamont | 73/864.73 X |
| 3,382,721 | 5/1968 | Tinkham et al. | |
| 3,481,200 | 12/1969 | Lüdecke et al. | |
| 3,638,500 | 2/1972 | Wetzel | 73/864.31 X |
| 4,140,006 | 2/1979 | d'Auzac et al. | 73/863.23 |
| 5,146,796 | 9/1992 | Mailliet et al. | 73/864.73 X |

FOREIGN PATENT DOCUMENTS

2833340A1  2/1979  Germany.

*Primary Examiner*—Thomas P. Noland
*Attorney, Agent, or Firm*—Poms, Smith, Lande & Rose

[57] ABSTRACT

A sampling probe for sampling the exhaust gases of internal combustion engines, particularly commercial vehicles. The probe includes a sampling tube having an inlet at one end for receiving the gaseous products. The tube is pivoted to an arm at an outer end of the arm so that the sampling tube can move relative to the arm and manipulate the position of the inlet and insert the inlet into a gas outlet tube. The arm may be clamped to the gas outlet tube by a clamping arrangement operated from the end of the arm.

6 Claims, 1 Drawing Sheet

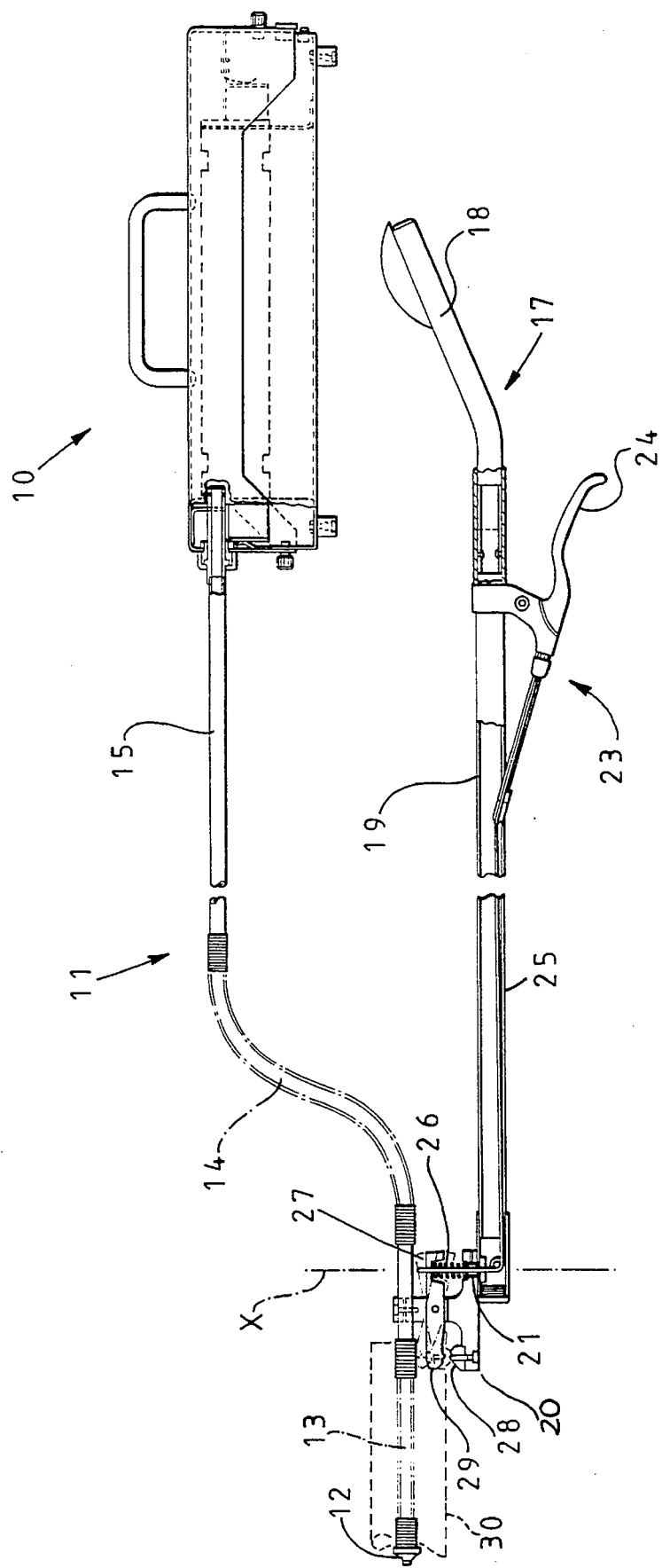

GAS SAMPLING PROBE

BACKGROUND OF THE INVENTION

This invention relates to sampling probes and, in particular but not exclusively, to probes for use for gaseous products, for example, in sampling the exhaust gases of engines.

Road vehicle exhaust gases need to be sampled to establish whether they comply with requirements that they be clean, but to gain access to the exhaust outlet for such gases is not always easy. This is particularly the case with goods vehicles.

SUMMARY OF THE INVENTION

It is an object of the invention to provide a sampling probe by which samples of gaseous products may be taken from relatively inaccessible outlet positions.

According to the invention a sampling probe for gaseous products comprises a sampling tube having an inlet for gaseous products at one end, an arm for supporting the tube and having an inner and an outer end, pivot means between the tube and the arm, and located towards the outer end of the arm so that the tube is pivotable relative to the arm to manipulate the position of the sampling tube inlet by relative movement between the arm and the tube, said inlet being located outwardly of said pivot means.

Preferably the probe includes clamping means located towards the outer end of the arm whereby the probe is clamped to an outlet for gaseous products to be sampled.

Conveniently the clamping means is operable remotely from said outer end of the arm by operating means and said operating means is located adjacent a handle at said inner end of same arm.

The clamping means may include clamping surfaces resiliently urged towards one another, the surfaces being movable apart by said operating means.

In sampling the exhaust gases of vehicles the sampling tube is connected to measuring means whereby the smoke content of the gaseous products is measured.

Conveniently the sampling tube includes a flexible portion located inwardly of the pivot means and a rigid portion associated with the pivot means whereby the inlet end of the tube is movable relative to the arm.

Preferably the pivot means and the clamping means form part of the same unit.

In one arrangement the length of said rigid portion, the location of said tube inlet, the position of said pivot means and the length of the arm are arranged to enable the inlet end to be inserted into a tubular exhaust member through which the gaseous products are discharged and in which said products are sampled by admission to said inlet end for passage along the tube to measuring means, the tubular member being clampable to said arm.

BRIEF DESCRIPTION OF THE DRAWING

Further features of the invention will appear from the following description of an embodiment given by way of example only and with reference to the accompanying drawing, which shows a side elevation of a sampling probe assembly.

DETAILED DESCRIPTION OF PREFERRED EMBODIMENTS

In the illustrated arrangement the sampling probe is intended to sample the exhaust gases of internal combustion engines to establish the smoke content of the gases. Analysis of the smoke content is conducted in a sampling device 10, the detailed construction of which does not form part of the present invention but may be of the kind described in our British patent application No. 9214110.0

The sampling device 10 is provided with an exhaust gas sample through a sampling tube 11 having an inlet end 12 formed at one end of a rigidly constructed portion 13. A flexibly constructed portion 14 communicates with the portion 13 and with a further rigid portion 15 which, in turn, communicates with the sampling device 10.

There is also provided an arm 17 having a handle 18 at one end, a rigid tube 19 extending from the handle 18 and at the end of the tube 19 remote from the handle 18 is provided a clamping device 20 and a pivot 21. As shown in the drawing the pivot 21 is secured to the rigid part 13 of the tube 11 at a position spaced from the inlet end 12 of the sampling tube 11. By provision of the pivot 21 the tube part 13 may pivot about an axis X transverse to the longitudinal axis of the part 13 and relative to the arm 17.

The clamping means 20 is operated by a trigger mechanism 23 in the manner of a bicycle brake using a movable trigger 24 to draw a wire 25 along the tube 19 and against a spring 26 of the clamping means 20. The spring 26 urges a clamping arm 27 so that a clamping surface 29 at the opposite end of the arm 27 is urged towards a fixed clamping surface 28 of the clamping means 20. It will be seen that upon operation of the trigger 24 the clamping surfaces 28 and 29 are moved apart to enable an outlet 30 for the exhaust gases to be received therebetween. Such an outlet is shown at 30 consisting of a vehicle exhaust pipe into which the inlet end 12 of the sampling tube 11 is inserted. Upon release of the trigger 24 the outlet pipe 30 is clamped between the surfaces 28 and 29.

In use the inlet end of the sampling tube 11 needs to be inserted into an outlet pipe 30 which may be inaccessibly located under a vehicle of extending to a high point on the vehicle. By the use of the probe arrangement described and by manipulating the arm 17 to pivot the tube portion 13 relative to the arm it is possible to cause the inlet 12 to enter the outlet pipe 30 even if it lies at an angle to the direction of approach. The arm 17 and the sampling tube 11 may be moved relative to one another during the manipulation operation through the pivot action about the axis X. The length of the arm 17 and the relative length of the tube portions 13, 14 and 15 are arranged to reach and gain access to the pipe 30.

I claim:

1. A sampling probe for gaseous products, comprising:
   a sampling tube having an inlet for gaseous products at one end;
   an arm for supporting the tube and having an inner and an outer end;
   pivot means between the tube and the arm and located towards the outer end of the arm so that the tube is pivotable relative to the arm to manipulate the position of the sampling tube inlet by relative movement between the arm and the tube;
   the inlet being located outwardly of the pivot means; and
   the sampling tube including a flexible portion located inwardly of the pivot means and a rigid portion associated with the pivot means whereby the inlet end of the tube is moveable relative to the arm.

2. A sampling probe according to claim 1 comprising clamping means located towards the outer end of the arm whereby the probe is clamped to an outlet for gaseous products to be sampled.

3. A sampling probe according to claim 2 wherein the clamping means is operable remotely from said outer end of the arm by operating means, and said operating means is located adjacent a handle at said inner end of said arm.

4. A sampling probe according to claim 3 wherein said clamping means includes clamping surfaces resiliently urged towards one another, the surfaces being movable apart by said operating means.

5. A sampling probe according to claim 1 wherein the length of said rigid portion, the location of said tube inlet, the position of said pivot means and the length of the arm are arranged to enable the inlet end to be inserted into a tubular member through which the gaseous products are discharged and in which said products are sampled by admission of the products into said inlet end for passage along the tube to measuring means, the tubular member being clampable to said arm.

6. A sampling probe for gaseous products, comprising:

a sampling tube having an inlet for gaseous products at one end;

an arm for supporting the tube and having an inner and an outer end;

pivot means between the tube and the arm and located towards the outer end of the arm so that the tube is pivotable relative to the arm to manipulate the position of the sampling tube inlet by relative movement between the arm and the tube;

the inlet being located outwardly of the pivot means; and clamping means located towards the outer end of the arm whereby the probe is clamped to an outlet for gaseous products to be sampled, and the clamping means is operable remotely from the outer end of the arm by operating means, which is located adjacent a handle at the inner end of the arm.

* * * * *